US010055635B2

(12) United States Patent
Liu et al.

(10) Patent No.: US 10,055,635 B2
(45) Date of Patent: Aug. 21, 2018

(54) ARRAY SUBSTRATE, METHOD FOR DRIVING SAME, DISPLAY PANEL AND DISPLAY APPARATUS

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Yingming Liu, Beijing (CN); Xue Dong, Beijing (CN); Haisheng Wang, Beijing (CN); Xiaochuan Chen, Beijing (CN); Weijie Zhao, Beijing (CN); Changfeng Li, Beijing (CN); Xiaoliang Ding, Beijing (CN); Shengji Yang, Beijing (CN); Hongjuan Liu, Beijing (CN); Lei Wang, Beijing (CN); Wei Liu, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 87 days.

(21) Appl. No.: 15/327,025

(22) PCT Filed: Dec. 21, 2015

(86) PCT No.: PCT/CN2015/098044
§ 371 (c)(1),
(2) Date: Jan. 17, 2017

(87) PCT Pub. No.: WO2017/012259
PCT Pub. Date: Jan. 26, 2017

(65) Prior Publication Data
US 2018/0211086 A1 Jul. 26, 2018

(30) Foreign Application Priority Data

Jul. 21, 2015 (CN) .......................... 2015 1 0432400

(51) Int. Cl.
G06K 9/00 (2006.01)

(52) U.S. Cl.
CPC ................................. *G06K 9/0004* (2013.01)

(58) Field of Classification Search
CPC ........................... G06K 9/0004; G06F 3/0412
See application file for complete search history.

(56) References Cited

U.S. PATENT DOCUMENTS

2002/0052192 A1* 5/2002 Yamazaki ............ G06K 9/0004
455/411
2005/0139751 A1 6/2005 Park et al.
(Continued)

FOREIGN PATENT DOCUMENTS

CN 101714043 A 5/2010
CN 103019476 A 4/2013
(Continued)

OTHER PUBLICATIONS

First Chinese Office Action, for Chinese Patent Application No. 201610966562.0, dated Aug. 1, 2017, 10 pages.
(Continued)

*Primary Examiner* — David F Dunphy
(74) *Attorney, Agent, or Firm* — Kinney & Lange, P.A.

(57) ABSTRACT

The embodiments of the present disclosure provide an array substrate, a method for driving the array substrate, a display panel and a display apparatus. The array substrate comprises: a plurality of repetition units each comprising a plurality of sub-pixels, one of the plurality of sub-pixels having a palm print recognition unit, each sub-pixel having a display unit connected to a first scan line and a data line and configured to be turned on or off under control of the
(Continued)

30 Display Unit
40 Palm Print Recognition Unit first scan line, a data signal being inputted to the display unit from the data line while the display unit is on; and a touch control electrode connected to a touch control electrode line and configured to identify a touch control position. The palm print recognition unit is connected to a second scan line, a control voltage terminal and a read signal line, and configured to collect a palm print signal based on the touch control position identified by the touch control electrode under control of the control voltage terminal, and to output the collected palm print signal to the reach signal line under control of the second scan line.

20 Claims, 7 Drawing Sheets

(56) References Cited

U.S. PATENT DOCUMENTS

| | | | | |
|---|---|---|---|---|
| 2010/0156851 A1* | 6/2010 | Kurokawa | ............ | G06F 3/0412 345/175 |
| 2011/0109592 A1* | 5/2011 | Kurokawa | ............ | G06F 3/0412 345/175 |
| 2014/0340363 A1* | 11/2014 | Ikeda | .................... | G06F 3/0412 345/175 |
| 2014/0354823 A1* | 12/2014 | Kitchens | ................. | G06F 3/044 348/163 |
| 2015/0144945 A1 | 5/2015 | Kusunoki et al. | | |
| 2017/0017340 A1* | 1/2017 | Liu | ........................ | G06F 3/0416 |

FOREIGN PATENT DOCUMENTS

| | | |
|---|---|---|
| CN | 103838046 A | 6/2014 |
| CN | 104155785 A | 11/2014 |
| CN | 203930275 U | 11/2014 |
| CN | 104200768 A | 12/2014 |
| CN | 105093611 A | 11/2015 |
| CN | 204807869 U | 11/2015 |

OTHER PUBLICATIONS

International Search Report and Written Opinion (including English translation of Box V) dated Apr. 27, 2016, for corresponding PCT Application No. PCT/CN2015/098044.

English translation of the International Search Report and Written Opinion dated Apr. 27, 2016, for corresponding PCT Application No. PCT/CN2015/098044.

* cited by examiner

30 Display Unit
40 Palm Print Recognition Unit

At a first stage of that frame, input a scan signal to the first scan line Scan1 on a per line basis for enabling the corresponding display unit 30 on a per line basis, and input a data signal to the enabled display unit 30 via the data line DL, wherein in the first stage, the data signals inputted to the data lines DL are the same and are a bright picture signal — S021

At a second stage of that frame, collect a palm print signal using the palm print recognition unit 40 under control of the control voltage terminal V1, and input a scan signal to the second scan line Scan2 on a per line basis, such that the palm print recognition unit 40 connected to the second scan line Scan2 to which the scan signal is inputted currently outputs the collected palm print signal to the read signal line RL — S022

Fig. 8b

ARRAY SUBSTRATE, METHOD FOR DRIVING SAME, DISPLAY PANEL AND DISPLAY APPARATUS

CROSS-REFERENCE TO RELATED APPLICATIONS

The present disclosure corresponds to the PCT application PCT/CN2015/098044, and claims a benefit from the Chinese Patent Application No. 201510432400.4 filed on Jul. 21, 2015, which is incorporated herein by reference.

TECHNICAL FIELD

The present disclosure relates to display technology, and more particularly, to an array substrate, a method for driving the array substrate, a display panel and a display apparatus.

BACKGROUND

Liquid Crystal Displays (LCDs), with advantages including low radiation, small dimension and low energy consumption, have been widely applied in various electronic products such as tablet computers, televisions or mobile phones. Further, palm print recognition technique is of important significance for enhancing security of electronic devices and extending applications of electronic devices.

However, currently most of LCDs do not have such palm print recognition function, or are capable of palm print recognition with separate palm print recognition circuits added, which makes their structures complicated.

SUMMARY

The embodiments of the present disclosure provide an array substrate, a method for driving the array substrate, a display panel and a display apparatus, capable of providing the display apparatus with a palm print recognition function while having a simple structure.

In an aspect of the embodiments of the present disclosure, an array substrate is provided. The array substrate comprises: a plurality of repetition units each comprising a plurality of sub-pixels, one of the plurality of sub-pixels having a palm print recognition unit, each sub-pixel having a display unit connected to a first scan line and a data line and configured to be turned on or off under control of the first scan line, a data signal being inputted to the display unit from the data line while the display unit is on; and a touch control electrode connected to a touch control electrode line and configured to identify a touch control position. The palm print recognition unit is connected to a second scan line, a control voltage terminal and a read signal line, and configured to collect a palm print signal based on the touch control position identified by the touch control electrode under control of the control voltage terminal, and to output the collected palm print signal to the reach signal line under control of the second scan line.

Optionally, the display unit comprises a first transistor and a pixel electrode, the first transistor having its gate connected to the first scan line, its first electrode connected to the data line and its second electrode connected to the pixel electrode.

Optionally, the palm print recognition unit comprises a second transistor and a third transistor, the second transistor being a phototransistor. The second transistor has its gate and first electrode both connected to the control voltage terminal and its second electrode connected to a first electrode of the third transistor. The third transistor has its gate connected to the second scan line and its second electrode connected to the read signal line.

Optionally, the palm print recognition unit comprises a fourth transistor which is a phototransistor. The fourth transistor has its gate connected to the second scan line, its first electrode connected to the control voltage terminal and its second electrode connected to the read signal line.

Optionally, the palm print recognition unit comprises a fifth transistor which is a phototransistor. The fifth transistor has its gate connected to the second scan line, its first electrode connected to the control voltage terminal and its second electrode connected to the read signal line. For any line of the palm print recognition units, the control voltage terminals connected to the palm print recognition units in that line are connected to the second scan line.

Preferably, the palm print recognition unit is provided in a blue sub-pixel.

Preferably, at least one touch control electrode line and its corresponding read signal line are multiplexed in a time division manner.

In another aspect of the embodiments of the present disclosure, a display panel is provided. The display panel comprises the above array substrate.

In a further aspect of the embodiments of the present disclosure, a display apparatus is provided. The display apparatus comprises the above display panel and a signal receiving device connected to the read signal line. The signal receiving device is configured to receive the palm print signal outputted from the read signal line and recognize palm information based on the palm print signal.

In yet a further aspect of the embodiments of the present disclosure, a method for driving the above array substrate is provided. The method comprises: a touch control display stage for performing a cyclic scan of at least one frame until a preset gesture is detected; and a palm print recognition stage for performing a scan of one frame to obtain palm print information. The step of performing a cyclic scan of at least one frame comprises: at a first stage of the i-th frame, inputting a scan signal to the first scan line on a per line basis for enabling the corresponding display unit on a per line basis, and inputting a data signal to the enabled display unit via the data line; at a second stage of the i-th frame, inputting a touch control driving signal to the touch control electrode and receiving a touch control induction signal fed back from the touch control electrode, so as to identify the touch control position; determining whether the preset gesture has been detected based on the touch control positions identified from the first to i-th frames; and proceeding with the palm print recognition stage when the preset gesture has been detected, or performing a scan of the (i+1)-th frame in the touch control display stage when no preset gesture has been detected, where i is an integer larger than or equal to 1. The step of performing a scan of one frame in the palm print recognition stage comprises: at a first stage of that frame, inputting a scan signal to the first scan line on a per line basis for enabling the corresponding display unit on a per line basis, and inputting a data signal to the enabled display unit via the data line, wherein in the first stage, the data signals inputted to the data lines are the same and are a bright picture signal; at a second stage of that frame, collecting a palm print signal using the palm print recognition unit under control of the control voltage terminal, and inputting a scan signal to the second scan line on a per line basis, such that the palm print recognition unit connected to the second scan line to which the scan signal is inputted currently outputs the collected palm print signal to the read signal line.

The embodiments of the present disclosure provide an array substrate, a method for driving the array substrate, a display panel and a display apparatus. Under control of a first scan line, a data signal is inputted to a display unit via a data line, so as to achieve a normal image display function. By providing a touch control electrode, the array substrate has a touch control function. In this case, under control of a control voltage terminal and a second scan line, a palm print recognition unit collects a palm print signal for palm print recognition. Therefore, when the array substrate according to the embodiment of the present disclosure is applied in a display apparatus, the display apparatus has both a touch control display function and a palm print recognition function. When compared with the conventional solution in which palm print recognition is achieved by adding a separate palm print recognition circuit, the present disclosure provides a simpler structure.

BRIEF DESCRIPTION OF THE DRAWINGS

In order to illustrate the solutions according to the embodiments of the present disclosure or the conventional solutions clearly, the figures used for description of the embodiments or conventional solutions will be introduced briefly here. It is apparent to those skilled in the art that the figures described below only illustrate some embodiments of the present disclosure and other figures can be obtained from these figures without applying any inventive skills.

FIG. 8b shows an implementation of the step S02 in FIG. 7; and

DETAILED DESCRIPTION OF THE EMBODIMENTS

In the following, the solutions according to the embodiments of the present disclosure will be described clearly and fully with reference to the figures. Obviously, the embodiments described below are only some, rather than all, of the embodiments. Starting from the embodiments of the present disclosure, those skilled in the art can obtain other embodiments with applying any inventive skills. All these embodiments are to be encompassed by the scope of the present disclosure.

Unless indicated otherwise, any scientific or technical terminology used herein should be interpreted as what is commonly understood in the art. The terms "first", "second" and the like as used in the description and claims in the present disclosure do not imply any sequence, number or level of importance, but only serve to distinguish between different components. Likewise, the terms "one", "a" and the like do not indicate any limitation in amount, but the presence of at least one. The terms "connected to", "connected with" and the like do not imply any limitation to a physical or mechanical connection, but may refer to electrical connection, either direct or indirect.

Figure 1:
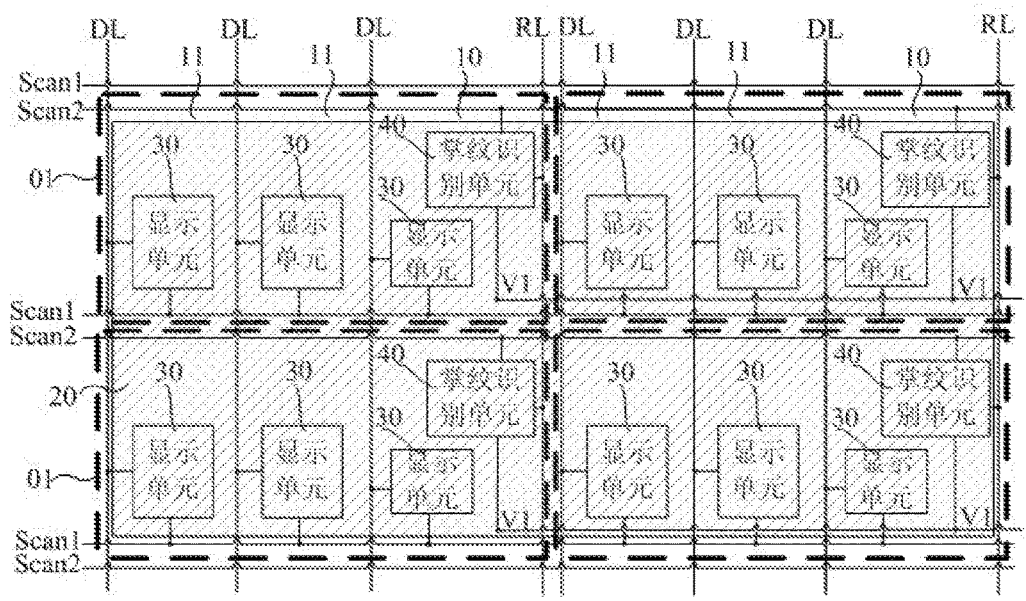
FIG. 1 is a first schematic diagram showing a structure of an array substrate according to an embodiment of the present disclosure.
Figure 2:
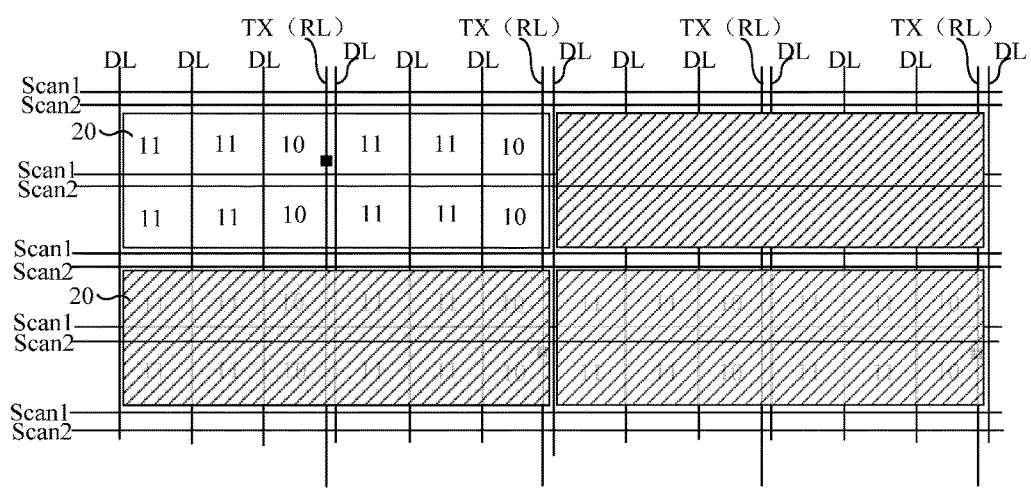
FIG. 2 is a second schematic diagram showing a structure of an array substrate according to an embodiment of the present disclosure.

According to an embodiment of the present disclosure, an array substrate is provided. FIG. 1 and FIG. 2 show a first and a second schematic diagrams each showing a structure of an array substrate according to an embodiment of the present disclosure, respectively. As shown in FIG. 1 and FIG. 2, the array substrate includes a plurality of repetition units 01. Each repetition unit 01 includes a plurality of sub-pixels each having a display unit 30. One of the sub-pixels has a palm print recognition unit 40. The array substrate further includes a touch control electrode 20 (the hatched parts in FIGS. 1 and 2) connected to a touch control electrode line TX.

In the embodiment of the present disclosure, for the purpose of illustration, the sub-pixel including the palm print recognition unit 40 is referred to as a first sub-pixel 10 and the remaining sub-pixels including a display unit 30 but no palm print recognition unit 40 are referred to as second sub-pixels 11.

Next, the structure of the array substrate according to the embodiment of the present disclosure will be described with reference to FIGS. 1 and 2.

As shown in FIG. 1, the display unit 30 is connected to a first scan line, Scan1, and a data line, DL, and is configured to be turned on or off under control of the first scan line Scan1. A data signal is inputted to the display unit from the data line DL while the display unit is on.

Here, preferably, the display units in each line are connected to one first scan line Scan1, and the display units in each column are connected to one data line DL.

The palm print recognition unit 40 is connected to a second scan line, Scan2, a control voltage terminal, V1, and a read signal line RL, and is configured to collect a palm print signal under control of the control voltage terminal V1, and to output the collected palm print signal to the reach signal line RL under control of the second scan line Scan2.

Here, preferably, the palm print recognition units 40 in each line are connected to one second scan line Scan2, and the palm print recognition units 40 in each column are connected to one read signal line RL.

Further, for any line of the palm print recognition units 40, the control voltage terminals V1 connected to the palm print recognition units 40 in that line are connected together via one connection line for providing the control voltage terminals V1 with a control signal. In this way, the number of connection lines can be reduced and the opening rate can be increased.

It is to be noted here that, first, the above palm print information is related to valley lines and ridge lines of a palm print. Second, the structure of the touch control electrode 20 is not limited to any specific structure, as long as the touch control function can be implemented. Third, the number of the second sub-pixels 11, other than the one first sub-pixel 10, in each repetition unit 01 can be selected depending on the distance between neighboring ridge lines in the palm print, the distance between neighboring valley lines in the palm print, and the size of each sub-pixel.

The embodiment of the present disclosure provides an array substrate. Under control of the first scan line Scan1, a data signal is inputted to the display unit 30 via the data line DL, so as to achieve a normal image display function. By providing the touch control electrode, the array substrate has a touch control function. In this case, under control of the control voltage terminal V1 and the second scan line Scan2, the palm print recognition unit 40 collects a palm print signal for palm print recognition. Therefore, when the array substrate is applied in a display apparatus, the display apparatus has both a touch control display function and a palm print recognition function. When compared with the conventional solution in which palm print recognition is achieved by adding a separate palm print recognition circuit, the present disclosure provides a simpler structure.

FIG. 2 is a second schematic diagram showing a structure of an array substrate according to an embodiment of the present disclosure. As shown in FIG. 2, preferably, at least one touch control electrode line TX and its corresponding read signal line RL are multiplexed in a time division manner. For example, from left to right, the first touch control electrode line TX and the first read signal line RL are multiplexed on a line, the third touch control electrode line TX and the third read signal line RL are multiplexed on a line, the fifth touch control electrode line TX and the fifth read signal line RL are multiplexed on a line, and so on. The present disclosure is not limited to any specific arrangement of multiplexing. In this way, the number of connection lines can be further reduced and the opening rate can be further increased. Further, in FIG. 2, each small black dot on the touch control electrode line TX indicates that the touch control electrode 20 and the touch control electrode line TX are connected with each other through a via.

Figure 3:
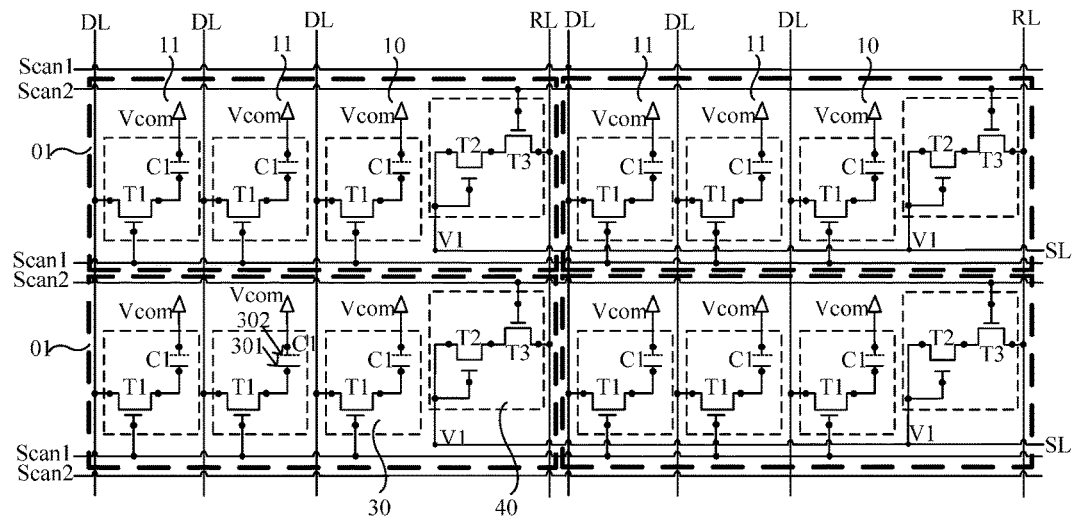
FIG. 3 is a schematic diagram showing specific structures of the respective units shown in FIG. 1.

FIG. 3 is a schematic diagram showing a specific structure of the array substrate shown in FIG. 1. As shown in FIG. 3, the display unit 30 can include a first transistor, T1, and a pixel electrode 301. The first transistor T1 has its gate connected to the first scan line Scan1, its first electrode connected to the data line DL and its second electrode connected to the pixel electrode 301.

In this case, a common electrode 302 can be provided on the array substrate or on a box substrate. The present disclosure is not limited to either of these arrangements. Here, the pixel electrode 301 and the common electrode 302 constitute a first capacitor C1, and the common electrode 302 is connected to a common voltage terminal, Vcom.

Preferably, the common electrode 302 can be provided on the array substrate, i.e., the display unit 30 may further include the common electrode 302.

As shown in FIG. 3, the palm print recognition unit 40 can include a second transistor, T2, and a third transistor, T3. The second transistor T2 is a phototransistor. The second transistor T2 has its gate and first electrode both connected to the control voltage terminal V1 and its second electrode connected to a first electrode of the third transistor T3. The third transistor T3 has its gate connected to the second scan line Scan2 and its second electrode connected to the read signal line RL.

Here, for any line of the palm print recognition units 40, the control voltage terminals V1 connected to the palm print recognition units 40 in that line are connected together via one signal line, SL, for providing the control voltage terminals V1 with a control signal.

Figure 4:
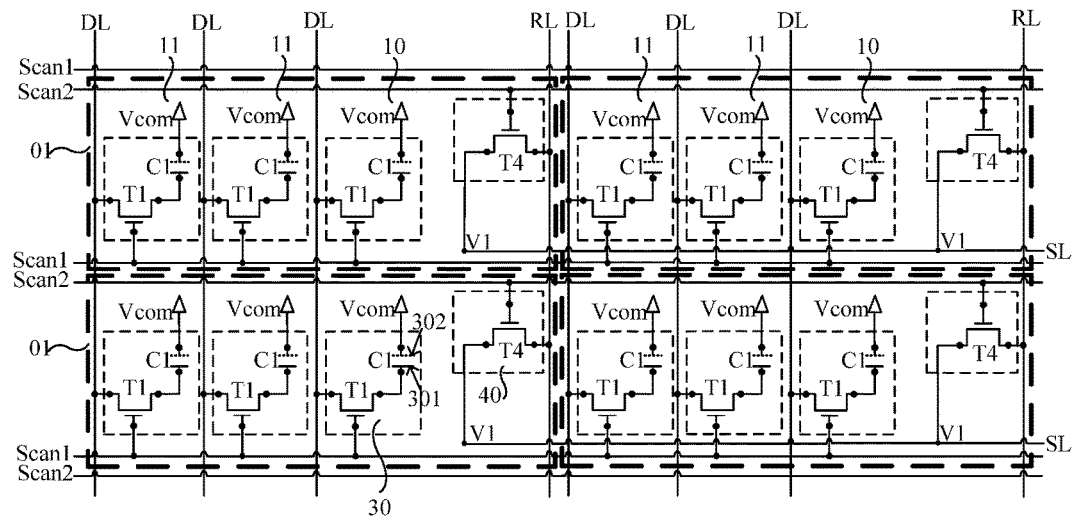
FIG. 4 is a schematic diagram showing specific structures of respective units in another array substrate according to another embodiment of the present disclosure.
Figure 5:
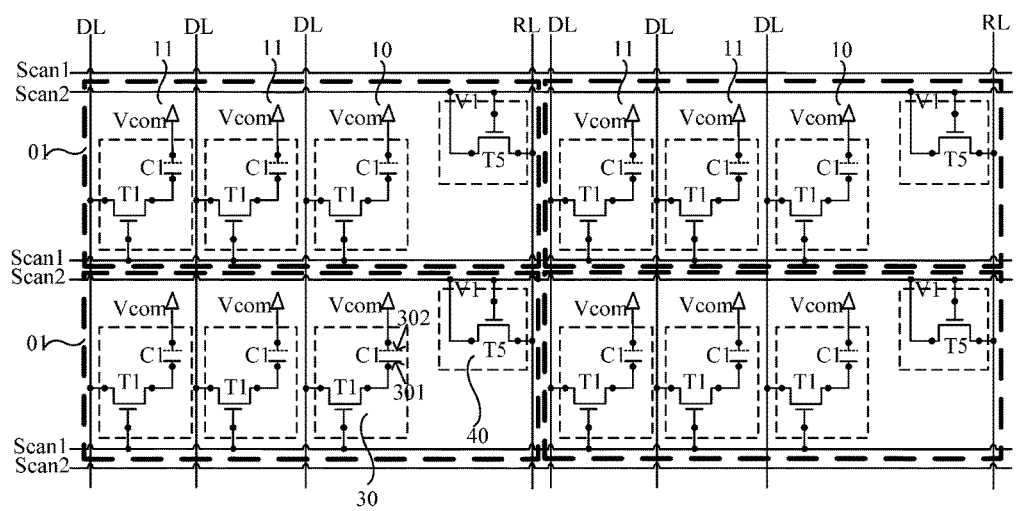
FIG. 5 is a schematic diagram showing specific structures of respective units in another array substrate according to yet another embodiment of the present disclosure.

If the leakage current from other lines connected to the read signal line RL has little influence on the detection current of the palm print recognition units 40 in the current line, the palm print recognition units may also have another structure as shown in FIG. 4 or 5.

FIG. 4 is a schematic diagram showing another specific structure of an array substrate according to an embodiment of the present disclosure. As shown in FIG. 4, the palm print recognition unit 40 can include a fourth transistor, T4, which is a phototransistor. The fourth transistor T4 has its gate connected to the second scan line Scan2, its first electrode connected to the control voltage terminal V1 and its second electrode connected to the read signal line RL.

Here, for any line of the palm print recognition units 40, the control voltage terminals V1 connected to the palm print recognition units 40 in that line are connected together via one signal line, SL, for providing the control voltage terminals V1 with a control signal.

FIG. 5 is a schematic diagram showing another specific structure of an array substrate according to an embodiment of the present disclosure. As shown in FIG. 5, the palm print recognition unit 40 can include a fifth transistor, T5, which is a phototransistor. The fifth transistor T5 has its gate connected to the second scan line Scan2, its first electrode connected to the control voltage terminal V1 and its second electrode connected to the read signal line RL.

For any line of the palm print recognition units 40, the control voltage terminals V1 connected to the palm print recognition units 40 in that line are connected to the second scan line Scan2.

In the embodiment of the present disclosure, the principle of palm print recognition by the palm print recognition unit 40 is as follows. In accordance with the refraction and reflection principle of light, when a palm touches a surface of a screen, a light source radiates light onto valley lines and ridge lines of the palm print. Since the valley lines and the ridge lines have different refraction angles and different reflection light intensities, they will cause different currents in a phototransistor. By inputting the currents to a reading device via the read signal line SL, the valley lines and ridge lines of the palm print can be recognized. Here, when the palm touches the screen, the ridge lines of the palm print are more easily in contact with the screen. In this case, when the light source radiates light to the ridge lines of the palm print, the full reflection on the surface is destroyed and the reflection light intensity is lowered. When the light source radiates light to the valley lines of the palm print, the light is fully reflected back.

Based on the above, since the distance between the ridge lines of the palm print is larger than 100 μm, the distance between the valley lines is larger than the distance between the ridge lines, and the side length of a pixel unit in the array substrate generally ranges from 50-90 μm, the size of the pixel unit is significantly smaller than the distance between a valley line and a ridge line in the palm print. Accordingly, in the embodiment of the present disclosure, preferably each pixel unit only includes one first sub-pixel 10. In this case, the pixel unit can include two second sub-pixel 11.

Further, since the blue light is most insusceptible to ambient environment among red, green and blue lights, in an embodiment of the present disclosure, the first sub-pixel 10 is preferably a blue sub-pixel. That is, in each pixel unit, the blue sub-pixel includes the palm print recognition unit 40 and the display unit 30, while each of the red sub-pixel and the green sub-pixel includes the display unit 30 but no palm print recognition unit 40.

It is to be noted that, in the embodiment of the present disclosure, the red sub-pixel, the green sub-pixel and the blue sub-pixel do not necessarily have a red, green or blue filter layer in the respective sub-pixels of the array substrate, as long as in the final display apparatus the red sub-pixel includes or corresponds to a red filter layer, the green sub-pixel includes or corresponds to a green filter layer, and the blue sub-pixel includes or corresponds to a blue filter layer. That is, the red filter layer can be provided in the sub-pixel of the array substrate or at a position corresponding to the sub-pixel in a color film substrate. The same also applies to other filter layers.

In the embodiments of the present disclosure, all the transistors can be N-type transistors or P-type transistors. All the embodiments of the present disclosure are described assuming all the transistors to be N-type transistors. Due to low leakage current of low-temperature poly-silicon thin-film transistor, it is preferably in the embodiments of the present disclosure that all the transistors are low-temperature poly-silicon thin-film transistors. Further, in the present disclosure, the first electrode can be a source and the second electrode can be a drain, or alternatively the first electrode can be a drain and the second electrode can be a source. The present disclosure is not limited to any of these arrangements.

According to an embodiment of the present disclosure, a display panel is also provided. The display panel includes the above array substrate and may further include a box substrate and a liquid crystal layer between the array substrate and the box substrate.

Further, according to an embodiment of the present disclosure, a display apparatus is provided. The display apparatus includes the above display panel and a signal receiving device 02 (as shown in FIG. 6) configured to receive the palm print signal outputted from the read signal line RL and recognize palm information based on the palm print signal.

Figure 6:
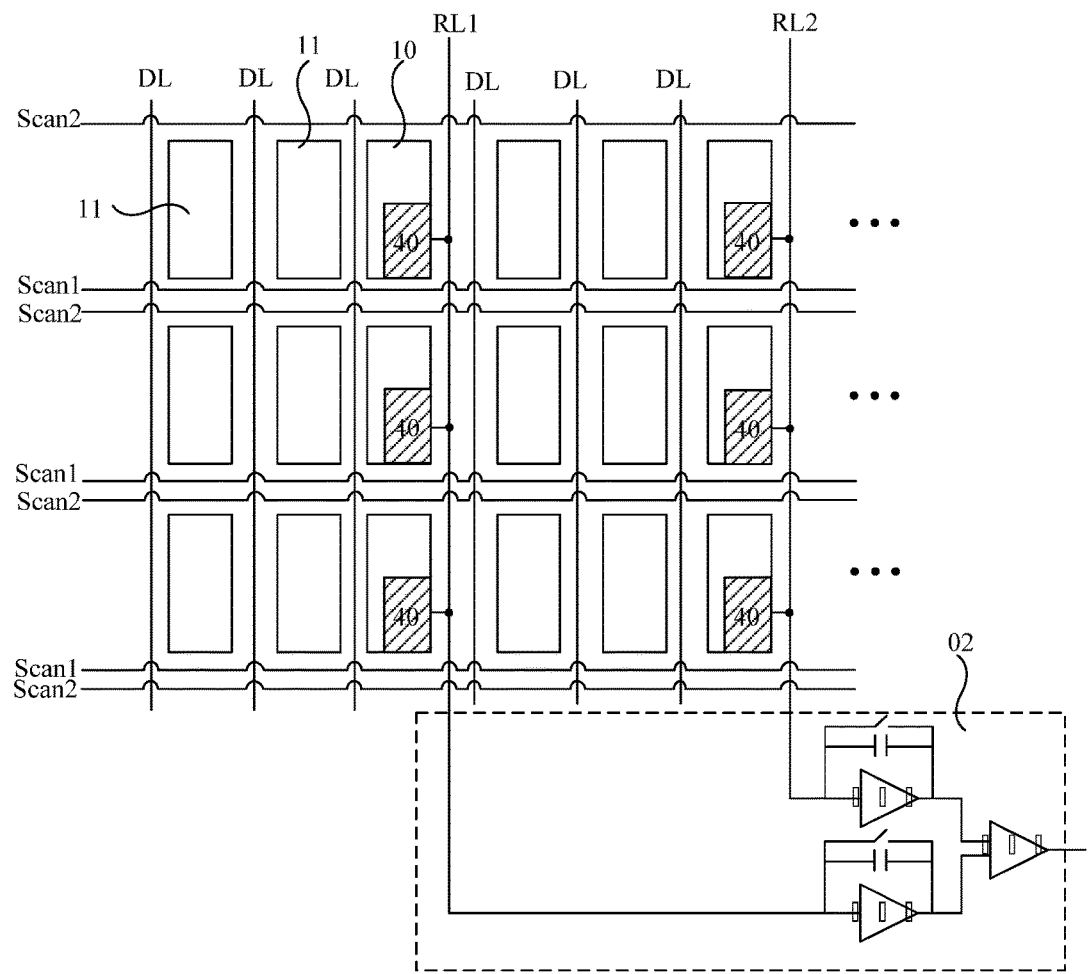
FIG. 6 is a schematic diagram showing a structure of a display apparatus according to an embodiment of the present disclosure.

In particular, the signal receiving device 02 can be connected to the palm print recognition units 40 in the first sub-pixels 10 in the first column and the palm print recognition units 40 in the first sub-pixels 10 in the second column, e.g., via the first read signal line RL1 and the second read signal line RL2 in FIG. 6, respectively. The receiving operation by the signal receiving device 02 will be detailed below.

For example, the signal receiving device 02 may include a plurality of amplifiers and a plurality of differentiators. Each amplifier has an input terminal connected to one read signal line RL. Each differentiator has input terminals connected to output terminals of two amplifiers whose input terminals are connected to any two neighboring read signal lines RL. The output terminal of each differentiator is configured to output a difference signal.

When the palm touches the screen, the phototransistor detects a change in light intensity and generates a current which is outputted via the read signal line RL to an amplifier of the signal receiving device 02 for amplification. The signals outputted from two neighboring read signal lines RL are amplified by the amplifier and then inputted to the input terminals of one differentiator. In this way, if the differentiator outputs a first difference which is positive, it can be determined that a valley line is collected by one of the read signal lines RL and a ridge line is collected by the other one of the read signal lines RL, or vice versa. If the differentiator outputs a second difference, it can be determined that both read signal lines RL collect valley lines or ridge lines. In this case, since each of these two read signal lines RL is connected to input terminals of another differentiator along with another neighboring read signal line RL, after amplification by another amplifier, it can be determined, in combination with the result from the other differentiator, whether the two read signal lines RL collect valley lines or ridge lines.

Further, based on the value outputted from the differentiator, a gray scale level it belongs to can be determined and a valley line or a ridge line having the corresponding gray scale can be displayed on the screen. However, the present disclosure is not limited to this.

Based on the above, in order to further improve the accuracy of recognition, instead of comparing signals obtained from two neighboring read signal lines RL, a signal obtained from any one read signal line RL can be compared with signals obtained from several nearby read signal lines RL. However, the present disclosure is not limited to this.

It is to be noted here that the palm print information typically includes main lines, wrinkles, dermal ridges, minutia points and triangulation points. Here, the main lines refer to several lines that are strongest and thickest on the palm. Most of palms have three main lines, referred to as life line, love line and wisdom line, respectively. Wrinkles are generally thinner and shallower than the main lines and are quite irregular. Minutia points, like fingerprints, are all over the palm. Triangulation points are central points of triangular areas formed by dermal ridges on the palm. These triangular areas are located below roots of the fingers and below the middle finder and near the wrist.

The above palm print information can be represented by valley lines and ridge lines. Hence, after the palm print information has been recognized using the display apparatus according to the present disclosure, the above palm print information can be extracted and then matched with palm print information stored in a database, so as to obtain a recognition result.

Figure 7:
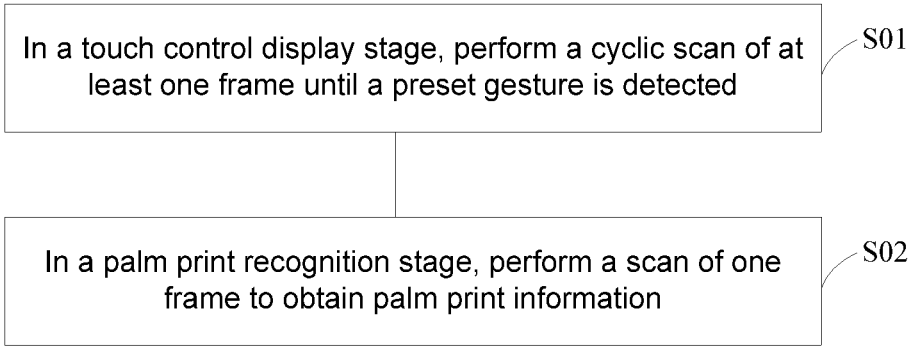
FIG. 7 is a flowchart illustrating a method for driving an array substrate according to an embodiment of the present disclosure.

According to an embodiment of the present disclosure, a method for driving the above array substrate is also provided. As shown in FIG. 7, the method can includes the following steps.

At step S01, in a touch control display stage, a cyclic scan of at least one frame is performed until a preset gesture is detected.

At step S02, in a palm print recognition stage, a scan of one frame is performed to obtain palm print information.

Figure 8A:
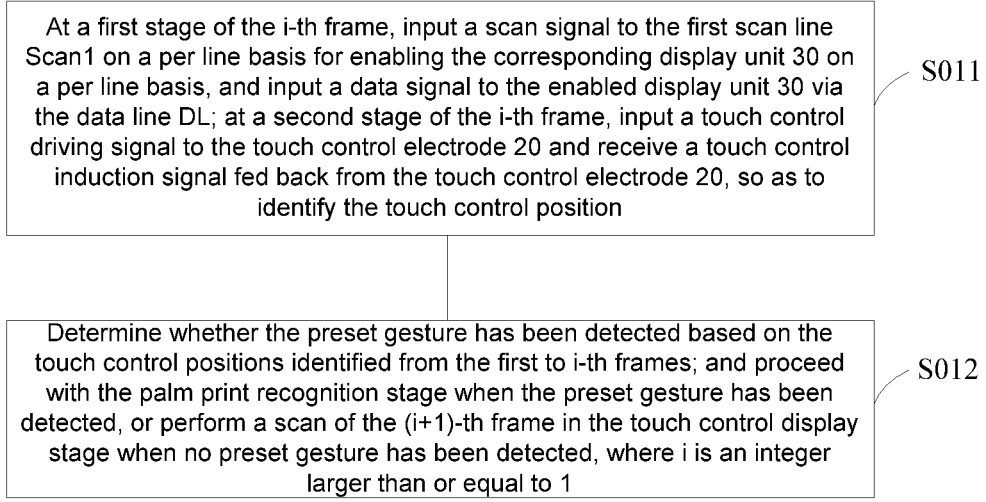
FIG. 8a shows an implementation of the step S01 in FIG. 7.

In particular, as shown in FIG. 8a, the step S01 may include the following steps.

At step S011, at a first stage of the i-th frame, a scan signal is inputted to the first scan line Scan1 on a per line basis for enabling the corresponding display unit 30 on a per line basis. A data signal is inputted to the enabled display unit via the data line DL. At a second stage of the i-th frame, a touch control driving signal is inputted to the touch control electrode 20 and a touch control induction signal fed back from the touch control electrode is received, so as to identify the touch control position.

At step S102, it is determined whether the preset gesture has been detected based on the touch control positions identified from the first to i-th frames. The method proceeds with the palm print recognition stage when the preset gesture has been detected, or a scan of the (i+1)-th frame in the touch control display stage is performed when no preset gesture has been detected, where i is an integer larger than or equal to 1.

In particular, as shown in FIG. 8b, the step S02 may include the following steps.

At step S021, at a first stage of that frame, a scan signal is inputted to the first scan line on a per line basis for enabling the corresponding display unit 30 on a per line basis. A data signal is inputted to the enabled display unit 30 via the data line DL. In the first stage, the data signals inputted to the data lines DL are the same and are a bright picture signal.

Here, the bright picture signal can be a white picture signal, a red picture signal, a green picture signal, a blue picture signal, or another picture perceived to be bright by human eyes.

At step S022, at a second stage of that frame, a palm print signal is collected using the palm print recognition unit 40 under control of the control voltage terminal V1. A scan signal is inputted to the second scan line Scan2 on a per line basis, such that the palm print recognition unit 40 connected to the second scan line Scan2 to which the scan signal is inputted currently outputs the collected palm print signal to the read signal line RL.

Figure 9:
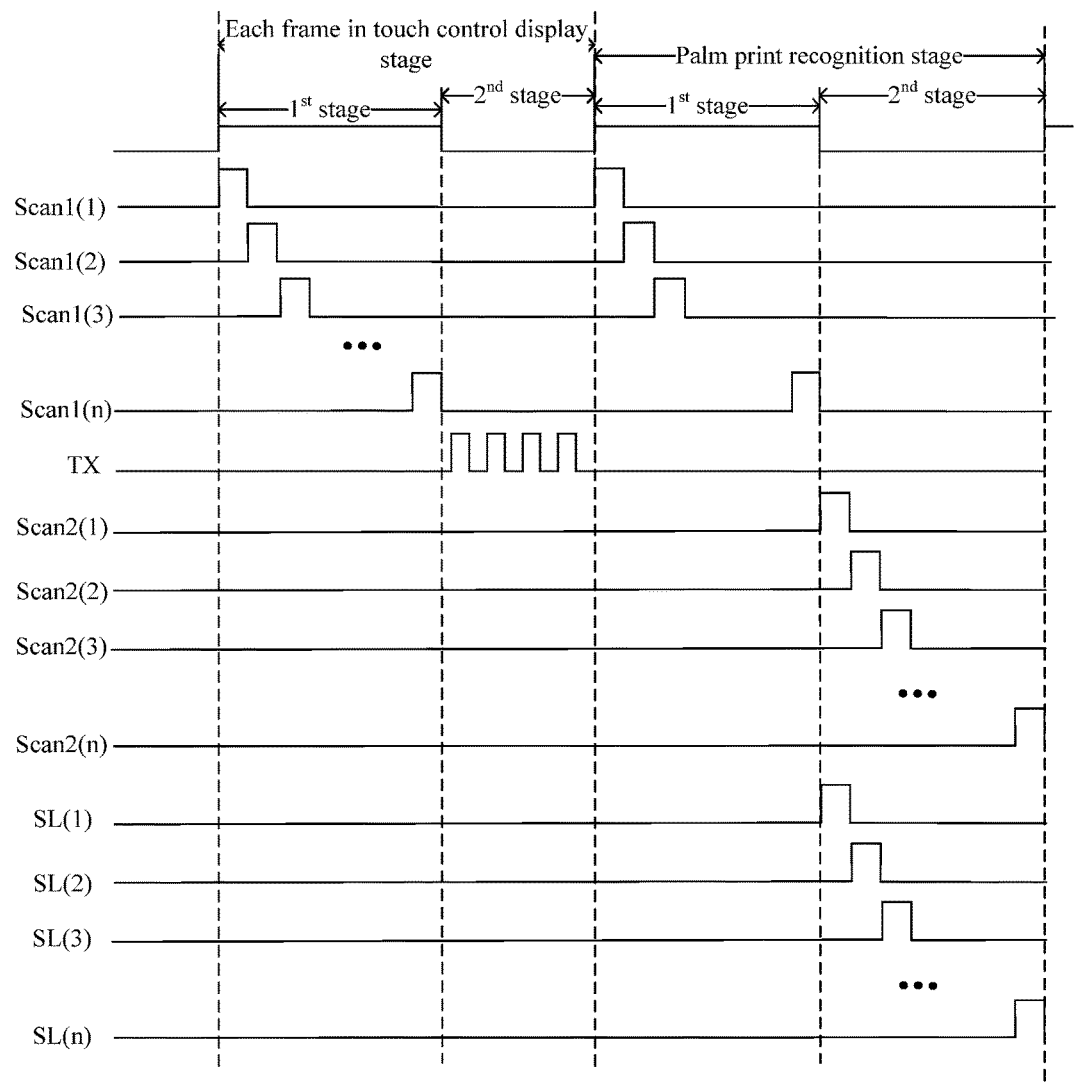
FIG. 9 is a sequence diagram of scan signals during operations of a display unit, a palm print recognition unit and a touch control electrode according to an embodiment of the present disclosure.

In the following, the operations of the display unit 30, the palm print recognition unit 40 and the touch control electrode 20 in the array substrate will be explained with reference to FIGS. 3 and 9. Here, all the transistors are assumed to be N-type transistors and the explanation will be given with reference to the sequence diagram shown in FIG. 9.

First, in a touch control display stage, a cyclic scan of at least one frame is performed until a preset gesture is detected. In particular, at the first stage of each frame in the touch control display stage, a scan signal is inputted to the first scan line Scan1 on a per line basis, such that the first transistor T1 connected to the first scan line Scan1 to which the scan signal is currently inputted is on. A signal inputted to the data line DL charges the terminal of the first capacitor C1 that is connected to the pixel electrode, so as to create a voltage difference between that terminal and the other terminal connected to the common electrode, thereby driving the liquid crystal to bias for displaying when the array substrate is applied in a display apparatus. In this way, when the scan of the first scan line Scan1 in the last line has completed, a frame of picture can be displayed.

At the second stage of each frame in the touch control display stage, a touch control driving signal is inputted to the touch control electrode line TX connected to the touch control electrode 20. There is a self-capacitance (Cp) formed between the touch control electrode 20 and the ground. Due to the effect of the electrical field of the human body, when the palm touches the screen, the capacitance of the palm will be added to the above self-capacitance, such that the value of the self-induced capacitance can be changed and the touch control position can be identified accordingly.

When the above cyclic scan of the at least one frame has completed, if it is determined that the preset gesture has been detected based on identified the touch control positions, the method proceeds with the palm print recognition stage. Here the preset gesture can be e.g., a finger sliding touch control.

At the first stage of the palm print recognition stage, a scan signal is inputted to the first scan line Scan1 on a per line basis, such that the first transistor T1 connected to the first scan line Scan1 to which the scan signal is currently inputted is on. Data signals of the same gray scale level are inputted to the data lines DL. At this stage, the signals inputted to the data lines DL are all the same. In this way, when the scan of the first scan line Scan1 in the last line has completed, a frame of a white picture can be displayed.

At the second stage of the palm print recognition stage, a scan signal is inputted to the second scan line Scan2 on a per line basis, such that the third transistor T3 connected to the second scan line Scan2 to which the scan signal is currently inputted is on. At the same time, a control signal is inputted to the signal line SL on a per line basis. When the palm touches the screen, under control of the control voltage terminal V1 connected to the signal line SL to which the control signal is currently inputted, if the second transistor T2 (a phototransistor) connected to the third transistor T3 in the on state receives light reflected from a ridge line, the light intensity is relatively low and its generated current is relatively small. If the second transistor T2 (a phototransistor) receives light reflected from a valley line, the light intensity is relatively high and its generated current is relatively large. The above current is outputted to the read signal line RL via the third transistor T3 in the on state.

Here, the signal line SL can be e.g., connected to a pin in an Integrated Circuit (IC) on the circuit board. The pin can provide the signal line SL with a fixed voltage signal or a pulse signal, depending on actual situations, as long as the signal it provides can enable the phototransistor to generate a current that varies as the light intensity varies, under control of the control voltage terminal V1 connected to the signal line SL.

In this way, after the scan of the second scan line Scan2 in the last line has completed, the palm print recognition unit 40 finishes the collection of the palm print signal, which is related to the valley lines and ridge lines of the palm print. When the second electrode of the second transistor T2 outputs a relatively small current, the collected palm print signal corresponds to a ridge line of the palm print. When the second electrode of the second transistor T2 outputs a relatively large current, the collected palm print signal corresponds to a valley line of the palm print. In this case, the outputted signal can be processed to obtain the palm print information (i.e., a valley or ridge line of the palm print).

Here, the second scan signal line Scan2 is a coordinate of the first sub-pixel 10 corresponding to the above palm print information (i.e., a valley or ridge line of the palm print in the horizontal axis, and the read signal line RL is a coordinate of the first sub-pixel 10 corresponding to the above palm print information (i.e., a valley or ridge line of the palm print in the vertical axis. With the above coordinates, the specific position on the screen corresponding to the palm print information can be determined. In this way, the palm print information matching the specific position can be displayed on the screen for the purpose of palm print recognition.

While the embodiments of the present disclosure have been described above, the scope of the present disclosure is not limited thereto. Various modifications and alternatives can be made by those skilled in the art without departing from the scope of the present disclosure. These modifications and alternatives are to be encompassed by the scope of the present disclosure, which is only defined by the claims as attached.

What is claimed is:

1. An array substrate, comprising:
    a plurality of repetition units each comprising a plurality of sub-pixels, one of the plurality of sub-pixels having a palm print recognition unit, each sub-pixel having a display unit connected to a first scan line and a data line and configured to be turned on or off under control of the first scan line, a data signal being inputted to the display unit from the data line while the display unit is on; and
    a touch control electrode connected to a touch control electrode line and configured to identify a touch control position, wherein the palm print recognition unit is connected to a second scan line, a control voltage terminal and a read signal line, and configured to collect a palm print signal based on the touch control position identified by the touch control electrode under control of the control voltage terminal, and to output the collected palm print signal to the read signal line under control of the second scan line.

2. The array substrate of claim 1, wherein the display unit comprises a first transistor and a pixel electrode, the first transistor having its gate connected to the first scan line, its first electrode connected to the data line and its second electrode connected to the pixel electrode.

3. A display panel, comprising the array substrate according to claim 2.

4. A display apparatus, comprising the display panel according to claim 3 and a signal receiving device connected to the read signal line,
wherein the signal receiving device is configured to receive the palm print signal outputted from the read signal line and recognize palm information based on the palm print signal.

5. The array substrate of claim 1, wherein the palm print recognition unit comprises a second transistor and a third transistor, the second transistor being a phototransistor,
wherein the second transistor has its gate and first electrode both connected to the control voltage terminal and its second electrode connected to a first electrode of the third transistor, and
the third transistor has its gate connected to the second scan line and its second electrode connected to the read signal line.

6. A display panel, comprising the array substrate according to claim 5.

7. A display apparatus, comprising the display panel according to claim 6 and a signal receiving device connected to the read signal line,
wherein the signal receiving device is configured to receive the palm print signal outputted from the read signal line and recognize palm information based on the palm print signal.

8. The array substrate of claim 1, wherein the palm print recognition unit comprises a fourth transistor which is a phototransistor,
wherein the fourth transistor has its gate connected to the second scan line, its first electrode connected to the control voltage terminal and its second electrode connected to the read signal line.

9. A display panel, comprising the array substrate according to claim 8.

10. A display apparatus, comprising the display panel according to claim 9 and a signal receiving device connected to the read signal line,
wherein the signal receiving device is configured to receive the palm print signal outputted from the read signal line and recognize palm information based on the palm print signal.

11. The array substrate of claim 1, wherein the palm print recognition unit comprises a fifth transistor which is a phototransistor,
wherein the fifth transistor has its gate connected to the second scan line, its first electrode connected to the control voltage terminal and its second electrode connected to the read signal line, and for any line of the palm print recognition units, the control voltage terminals connected to the palm print recognition units in that line are connected to the second scan line.

12. A display panel, comprising the array substrate according to claim 11.

13. A display apparatus, comprising the display panel according to claim 12 and a signal receiving device connected to the read signal line,
wherein the signal receiving device is configured to receive the palm print signal outputted from the read signal line and recognize palm information based on the palm print signal.

14. The array substrate of claim 1, wherein the palm print recognition unit is provided in a blue sub-pixel.

15. A display panel, comprising the array substrate according to claim 14.

16. The array substrate of claim 1, wherein at least one touch control electrode line and its corresponding read signal line are multiplexed in a time division manner.

17. A display panel, comprising the array substrate according to claim 16.

18. A display panel, comprising the array substrate according to claim 1.

19. A display apparatus, comprising the display panel according to claim 18 and a signal receiving device connected to the read signal line,
wherein the signal receiving device is configured to receive the palm print signal outputted from the read signal line and recognize palm information based on the palm print signal.

20. A method for driving the array substrate according to claim 1, comprising:
performing a cyclic scan of at least one frame with a touch control display stage until a preset gesture is detected; and
performing a scan of one frame with a palm print recognition stage to obtain palm print information,
wherein said performing a cyclic scan of at least one frame comprises: at a first stage of the i-th frame, inputting a scan signal to the first scan line on a per line basis for enabling the corresponding display unit on a per line basis, and inputting a data signal to the enabled display unit via the data line; at a second stage of the i-th frame, inputting a touch control driving signal to the touch control electrode and receiving a touch control induction signal fed back from the touch control electrode, so as to identify the touch control position; determining whether the preset gesture has been detected based on the touch control positions identified from the first to i-th frames; and proceeding with the palm print recognition stage when the preset gesture has been detected, or performing a scan of the (i+1)-th frame in the touch control display stage when no preset gesture has been detected, where i is an integer larger than or equal to 1, and
wherein said performing a scan of one frame in the palm print recognition stage comprises: at a first stage of that frame, inputting a scan signal to the first scan line on a per line basis for enabling the corresponding display unit on a per line basis, and inputting a data signal to the enabled display unit via the data line, wherein in the first stage, the data signals inputted to the data lines are the same and are a bright picture signal; at a second stage of that frame, collecting a palm print signal using the palm print recognition unit under control of the control voltage terminal, and inputting a scan signal to the second scan line on a per line basis, such that the palm print recognition unit connected to the second scan line to which the scan signal is inputted currently outputs the collected palm print signal to the read signal line.

* * * * *